(12) United States Patent
Canning et al.

(10) Patent No.: US 6,608,033 B1
(45) Date of Patent: Aug. 19, 2003

(54) TREATMENT OR PREVENTION OF COCCIDIOSIS

(75) Inventors: Peter C. Canning, Terre Haute, IN (US); Renee L. Hassfurther, Sullivan, IN (US); Nigel A. Evans, East Lyme, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/630,045

(22) Filed: Aug. 1, 2000

Related U.S. Application Data

(60) Provisional application No. 60/151,160, filed on Aug. 27, 1999.

(51) Int. Cl.[7] ................................................ A61K 31/70
(52) U.S. Cl. ........................................................ 514/29
(58) Field of Search ............................................ 514/29

(56) References Cited

U.S. PATENT DOCUMENTS

| 4,136,191 A | 1/1979 | Sakamoto |
| 4,820,695 A | 4/1989 | Debono et al. |
| 4,963,531 A | 10/1990 | Remington et al. |
| 5,574,020 A | 11/1996 | Klink et al. |

FOREIGN PATENT DOCUMENTS

| EP | 512779 A1 | 1/1992 |
| EP | 606747 A1 | 12/1993 |
| GB | 1061893 | 3/1967 |
| GB | 2232668 | 12/1990 |
| JP | 04095095 | 3/1992 |
| JP | 4095095 | 3/1992 |
| WO | 9841207 A1 | 3/1998 |
| WO | 9856802 A1 | 5/1998 |
| WO | 9856802 | 12/1998 |

OTHER PUBLICATIONS

Abstract, JP4095095 A, Mar. 27, 1992.
XP 002156026 Derwent Publications Ltd. AN 1992–156285.
EPO Search Report Jan. 4, 2001.

*Primary Examiner*—Ellie Peselev
(74) *Attorney, Agent, or Firm*—Peter C. Richardson; Gregg C. Benson; Christine S. Lee

(57) ABSTRACT

Coccidiosis in a bovine animal is prevented by administration of an effective amount of a macrolide antibiotic.

6 Claims, 11 Drawing Sheets

Mean daily rectal temperatures of calves administered either amprolium or the compound of Formula II (mean± SEM)

Mean daily attitude scores of calves treated with either amprolium or the compound of Formula II (mean± SEM).

Mean daily fecal consistency scores of calves administered either tilmicosin or amprolium (mean± SEM)

Mean daily oocyst shedding of calves administered either tilmicosin or amprolium (mean± SEM)

Speciation profiles of calves experimentally infected with three *Eimeria* species.

TREATMENT OR PREVENTION OF COCCIDIOSIS

This application claims priority under 35 U.S.C. §119(e) of U.S. application Ser. No. 60/151,160 filed Aug. 27, 1999, which application is hereby incorporated by reference herein.

FIELD OF THE INVENTION

The present invention relates to the treatment or prevention of coccidiosis in bovine animals that are susceptible to coccidia infection.

BACKGROUND OF THE INVENTION

Coccidiosis is an intestinal disease that affects several animal species. The disease, however, represents a particularly important problem in the raising of poultry and cattle.

In cattle, coccidiosis is primarily a disease of the young where there is crowding, stress, and/or nonimmune animals. Older cows act as a reservoir and shed oocysts into the environment. Shipping, weaning, dietary changes, and steroid therapy can precipitate coccidiosis. Even cattle immune to their own endemic species of coccidia can become ill when exposed to different species. Coccidiosis may result in death.

The causative agent is a protozoan that has the ability to rapidly multiply. Damage is incurred by the rapid multiplication of the parasite in, and the subsequent rupture of, cells of the intestinal lining. Several species of coccidia occur in cattle but *Eimeria zuemii* and *Eimeria bovis* are the most frequently isolated species associated with the disease.

Bovine coccidia undergo various stages of development. Infection gives rise to a microscopic egg (called an oocyst), which is passed out in manure. Under proper conditions, the oocyst develops within three to seven days to form a sporulate oocyst, which is capable of infecting other cattle. The sporulated oocyst contains eight bodies (called sporozoites), each of which is capable of entering a cell in the animal's intestine. When sporozoites enter intestinal cells, they divide several times, and each resulting offspring is capable of entering another intestinal cell. Male and female cells are produced. The male fertilizes the female to produce an oocyst, which in turn ruptures the intestinal cell and is passed in the manure. Thousands of oocysts may be passed in the manure of an infected animal.

Oocysts are resistant to environmental stresses and contaminate feed and water, infecting other animals. Ingestion of oocysts may not produce disease, since animals can carry them without being affected. Recovered animals develop immunity and are partially resistant to reinfection.

Several anticoccidial drugs are available for treatment or prevention of coccidiosis, including sulfonamides such as sulfaquinoxaline and sulfamethazine, amprolium, lasalocid decoquinate, and monensin. Drugs that are useful to treat coccidiosis are not necessarily useful to prevent the disease.

Drugs currently used for treatment or prevention of coccidiosis suffer from certain disadvantages. For example, monensin, a polyether ionophore that is administered in feed is sufficiently toxic that it must be gradually administered. Amprolium requires a complicated dosing regime.

Antibiotics have been employed to treat various infections in bovine cattle. For example, macrolide antibiotics are frequently administered to cattle at risk of developing respiratory infections upon arrival at a feedyard. Such antibiotics are advantageous in that they persist at high levels in blood and tissue, often achieving the desired preventive or therapeutic effect with only a single dose.

According to the present invention, macrolide antibiotics have been determined to be effective in the treatment or prevention of coccidiosis in bovine animals. The macrolide antibiotics are effective, for example, when administered prior to development of coccidiosis, at the time that such animals enter a feed lot and are exposed to stresses that may otherwise induce the disease.

That the antibiotics would be effective, e.g., in preventing coccidiosis in animals exposed to, or infected with, coccidia was not predictable. As noted above, the ability to prevent coccidiosis is not normally predictable even for agents known to treat the disease. Also, the mechanism by which the macrolide antibiotics might be found effective against Eimeria was not known.

SUMMARY OF THE INVENTION

The present invention relates to a method of treating or preventing coccidiosis in a bovine animal comprising administering to the mammal an effective amount of a macrolide antibiotic. Administration to prevent the disease is preferred. The antibiotic is preferably of the azalide class.

BRIEF DESCRIPTION OF THE DRAWINGS

Other advantages of the present invention will be readily appreciated as the same becomes better understood by reference to the following detailed description when considered in connection with the accompanying drawings, wherein.

DETAILED DESCRIPTION OF THE INVENTION

Figure 1:
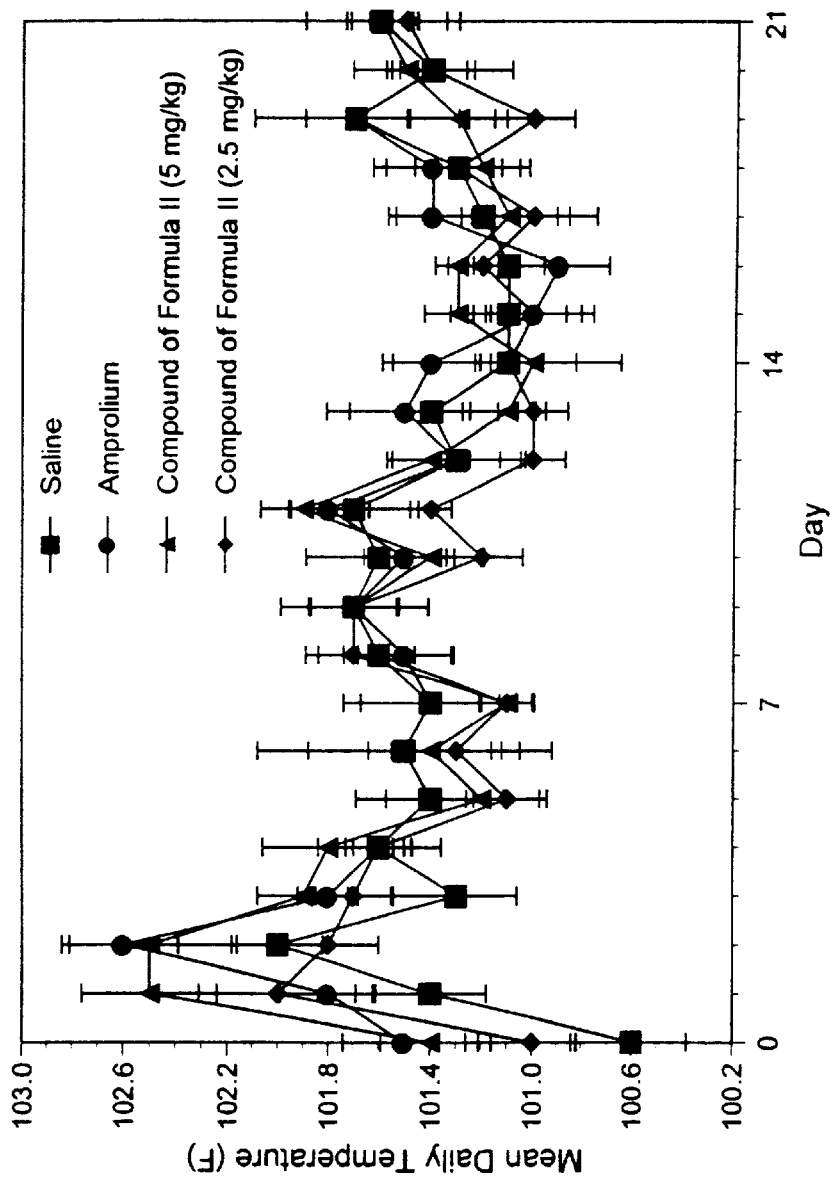
FIG. 1 shows the mean daily rectal temperatures of calves administered either amprolium or the compound of Formula II (mean±SEM)
Figure 2:
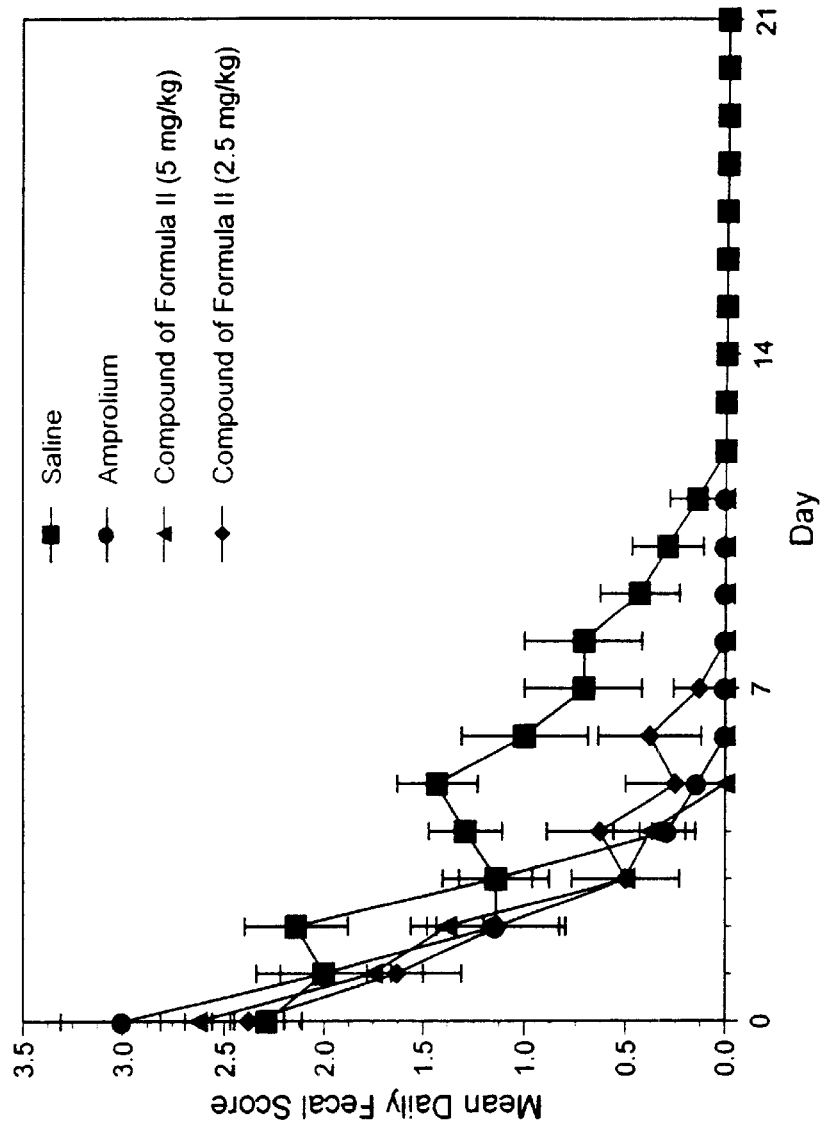
FIG. 2 shows the mean daily fecal scores of calves administered either amprolium or the compound of Formula II (mean±SEM)
Figure 3:
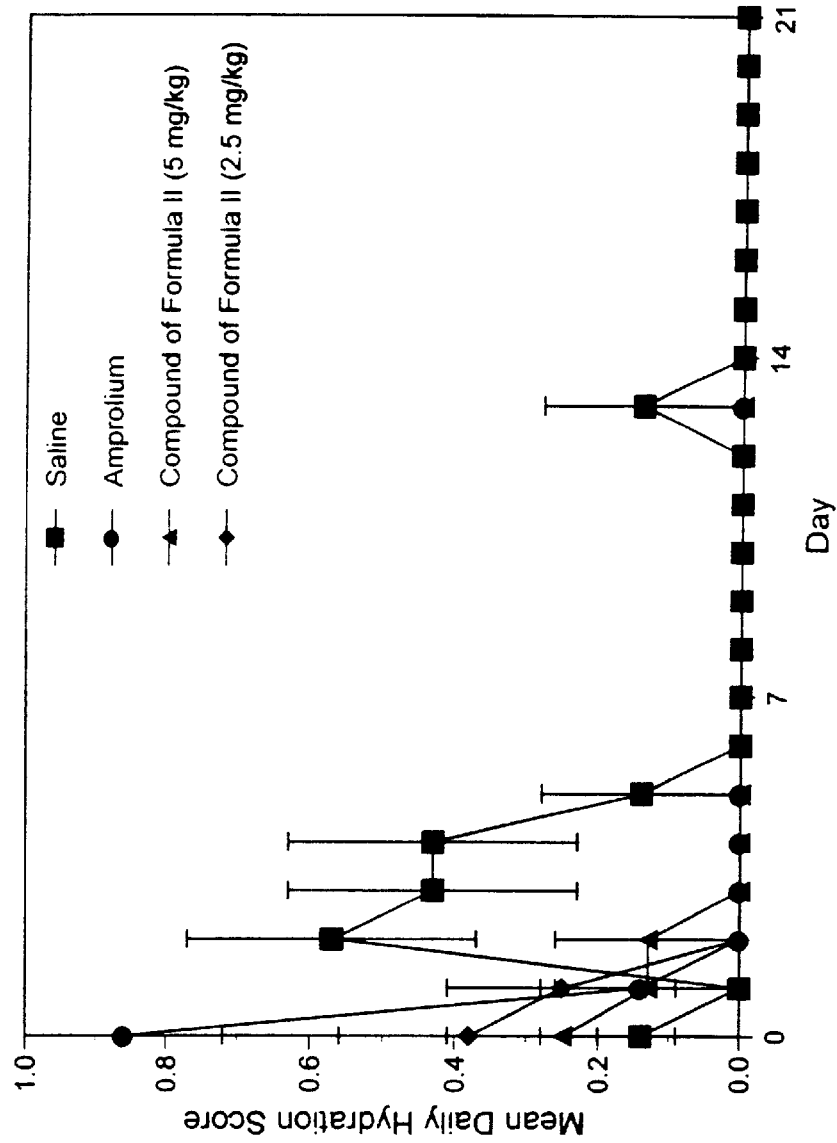
FIG. 3 shows the mean daily hydration scores of calves administered either amprolium or the compound of Formula II (mean±SEM)
Figure 4:
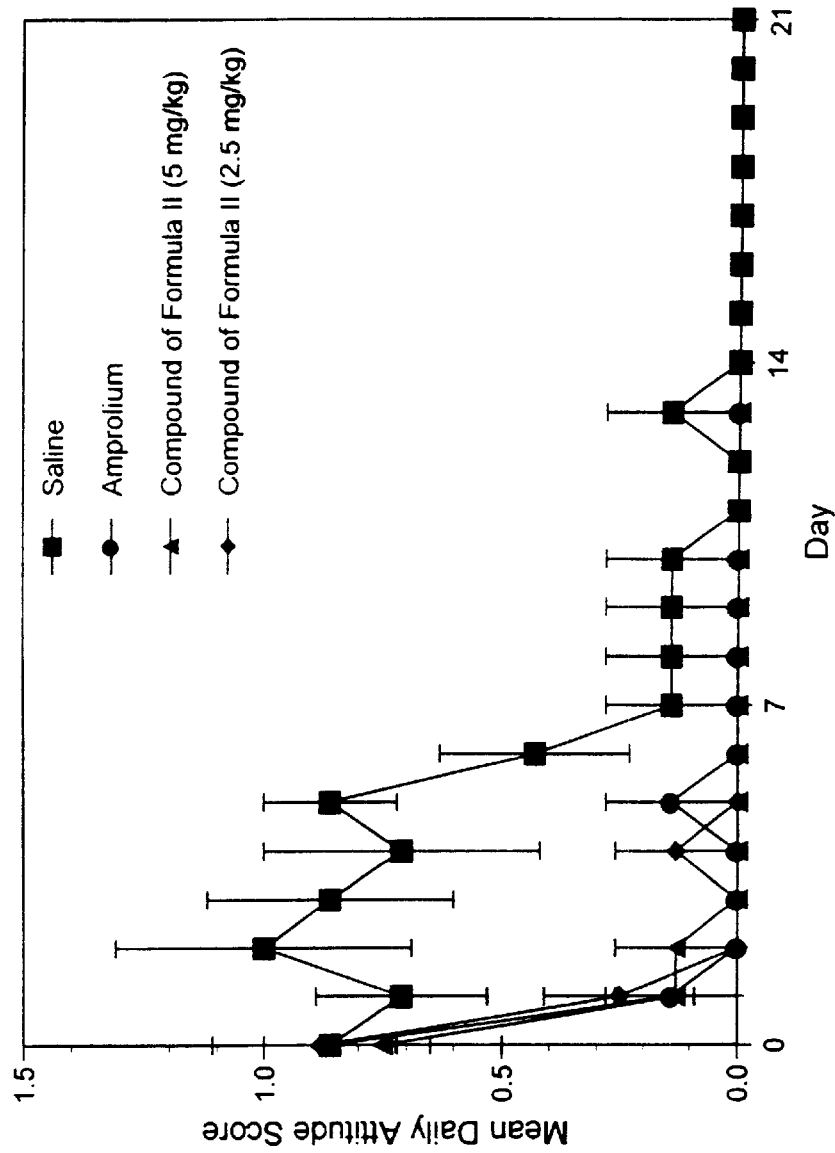
FIG. 4 shows the mean daily attitude scores of calves treated with either amprolium or the compound of Formula II (mean±SEM)
Figure 5:
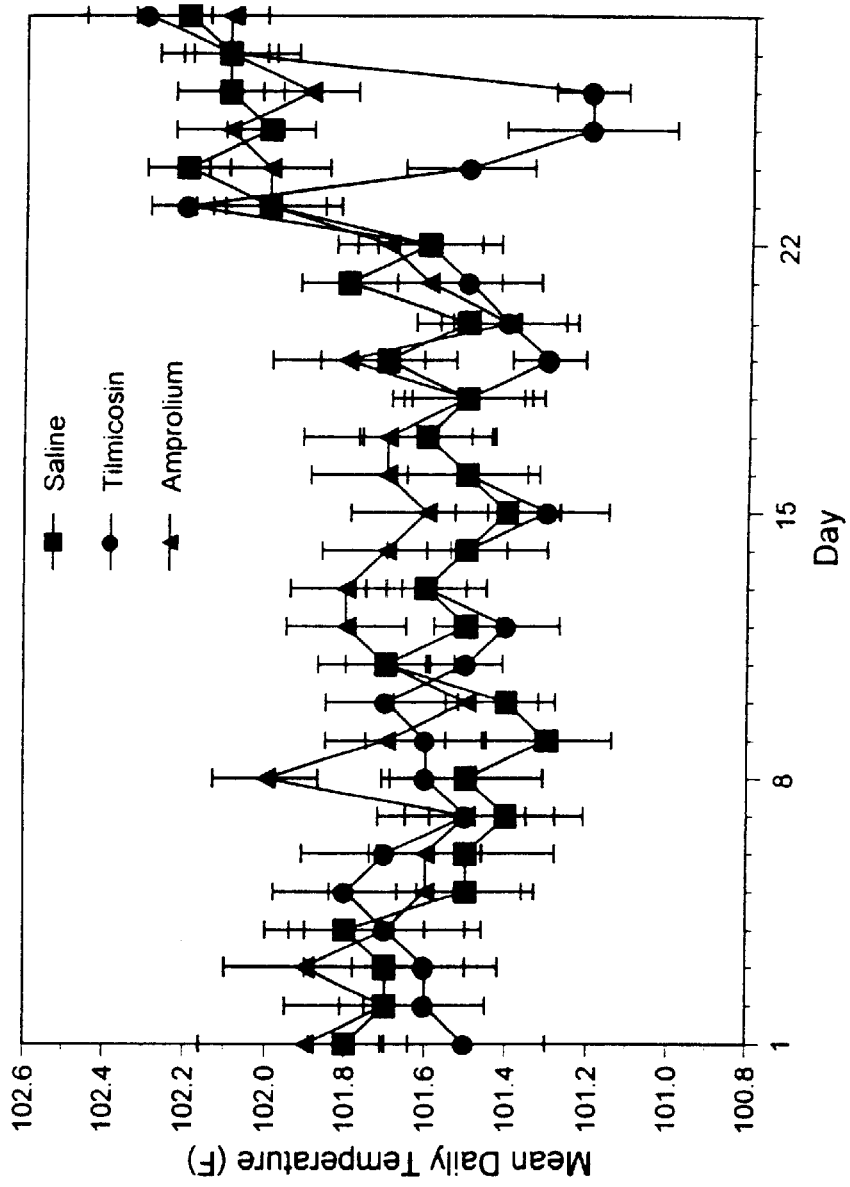
FIG. 5 shows the mean daily rectal temperatures of calves administered either tilmicosin or amprolium (mean±SEM)
Figure 6:
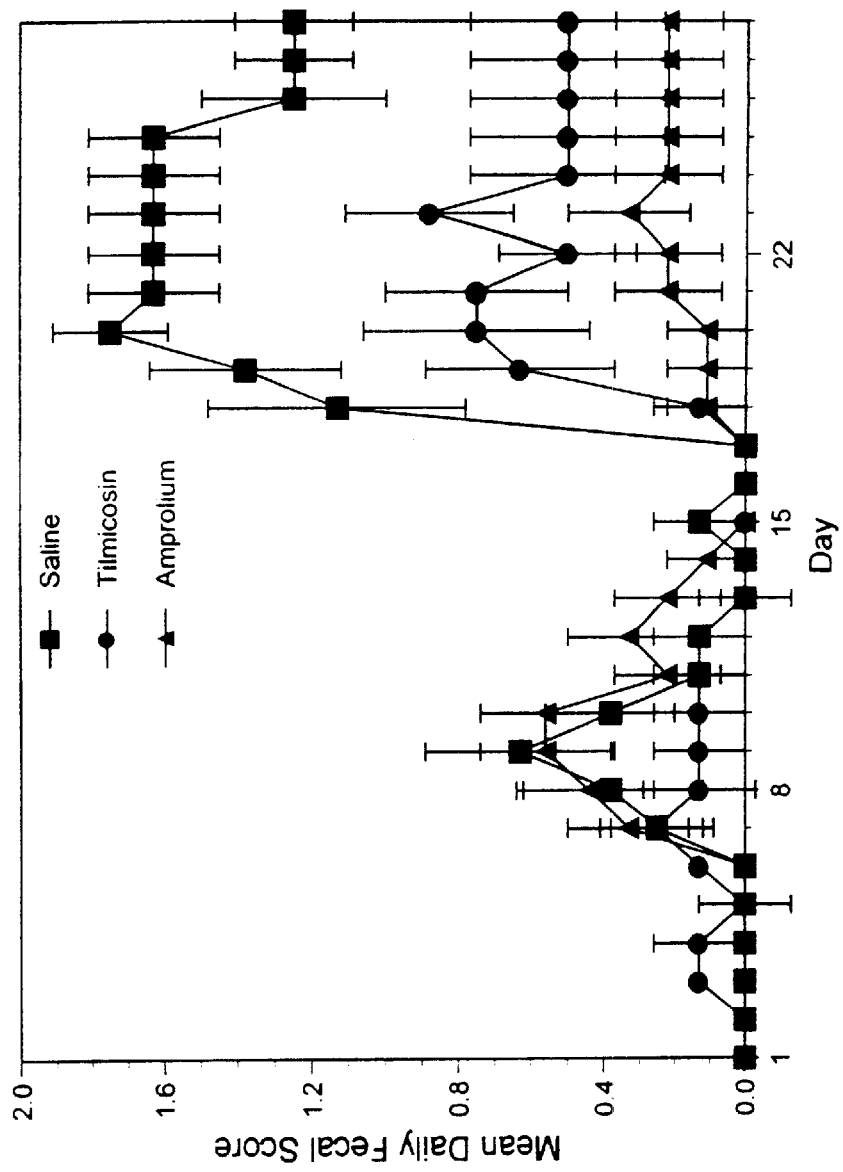
FIG. 6 shows the mean daily fecal consistency scores of calves administered either tilmicosin or amprolium (mean±SEM)
Figure 7:
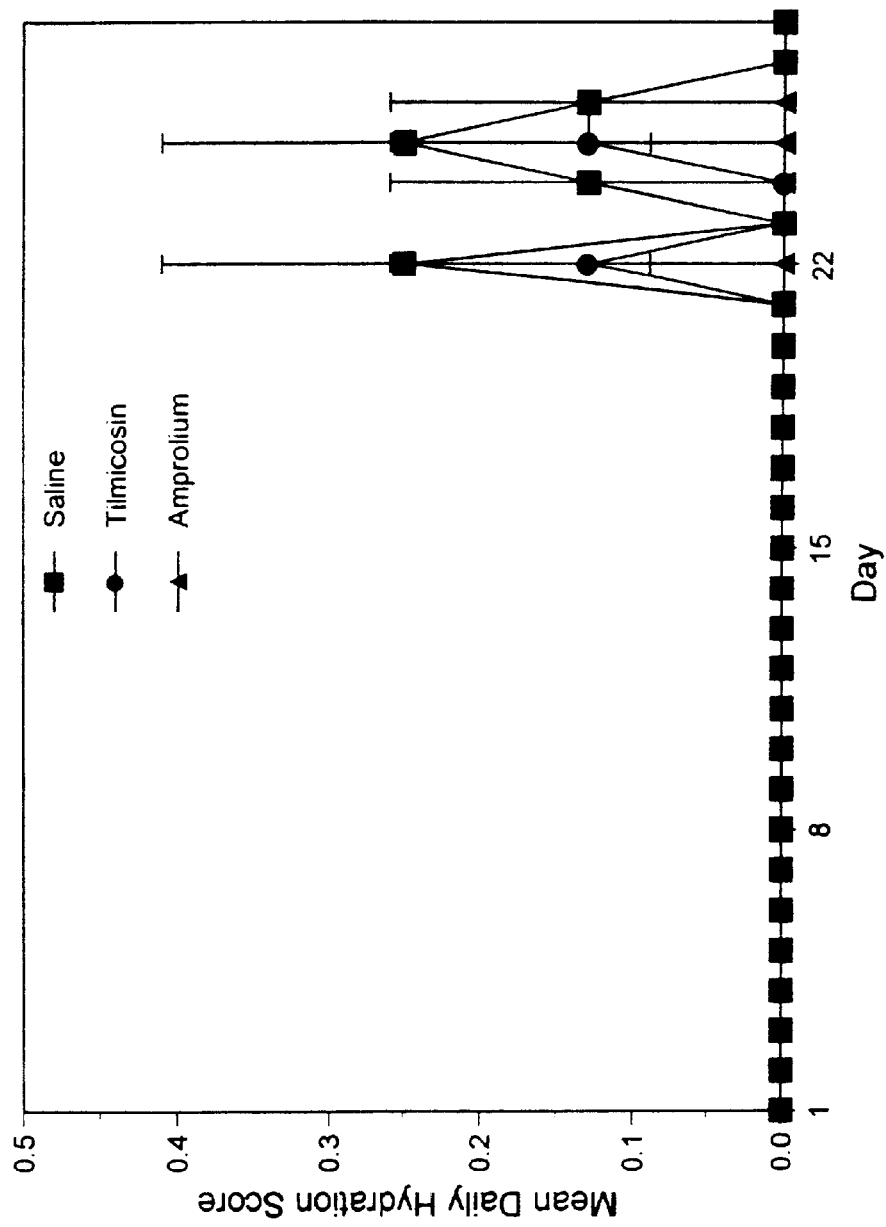
FIG. 7 shows the mean daily hydration scores of calves treated with either tilmicosin or amprolium (mean±SEM)
Figure 8:
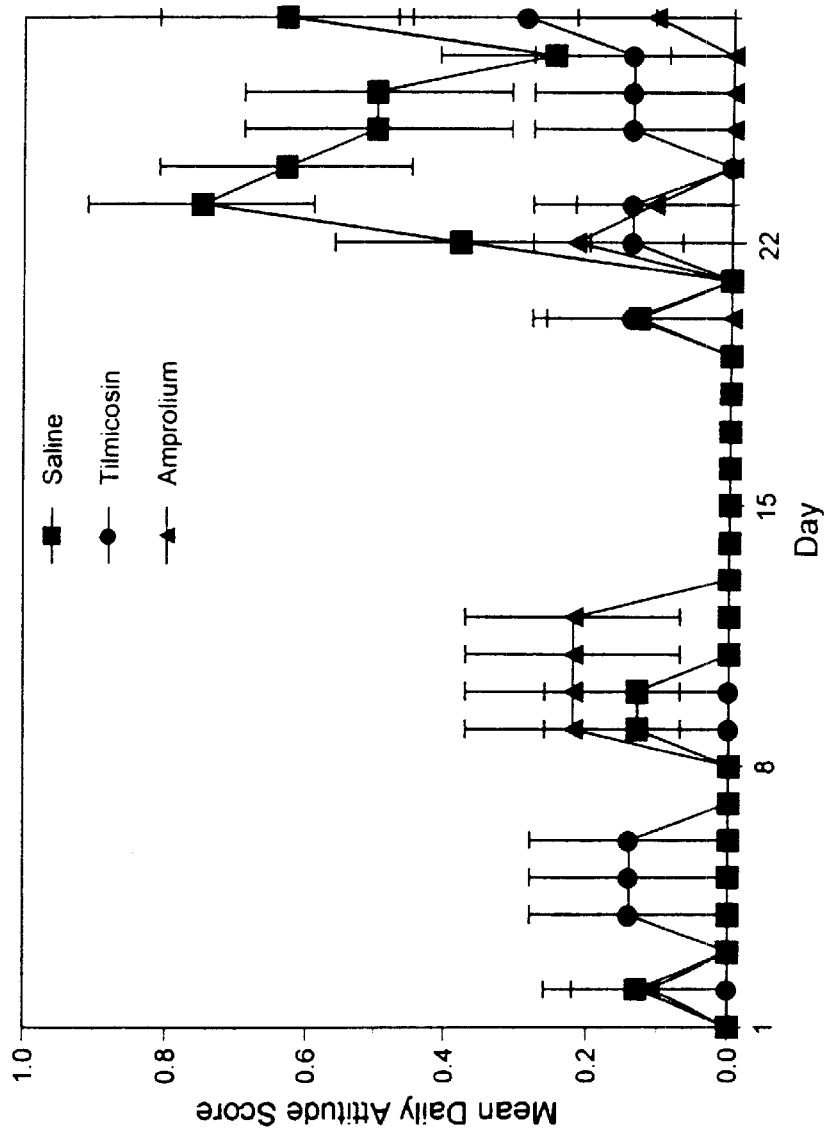
FIG. 8 shows the mean daily attitude scores of calves administered either tilmicosin or amprolium (mean±SEM)
Figure 9:
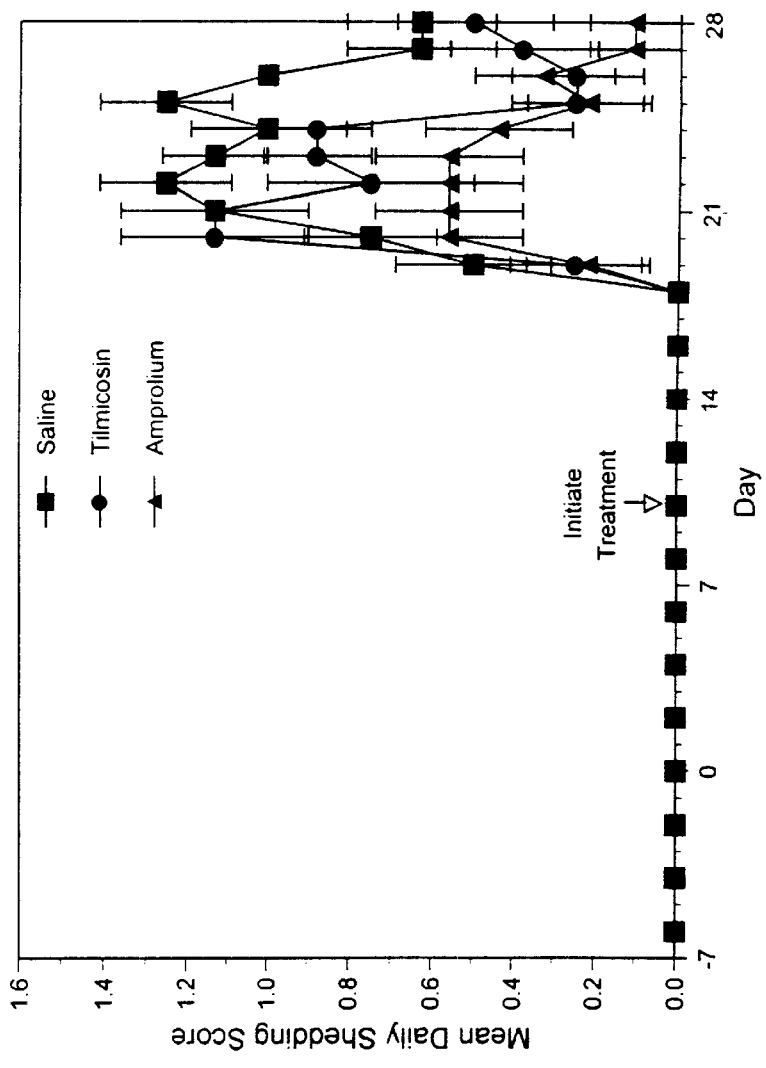
FIG. 9 shows the mean daily oocyst shedding of calves administered either tilmicosin or amprolium (mean±SEM)
Figure 10:
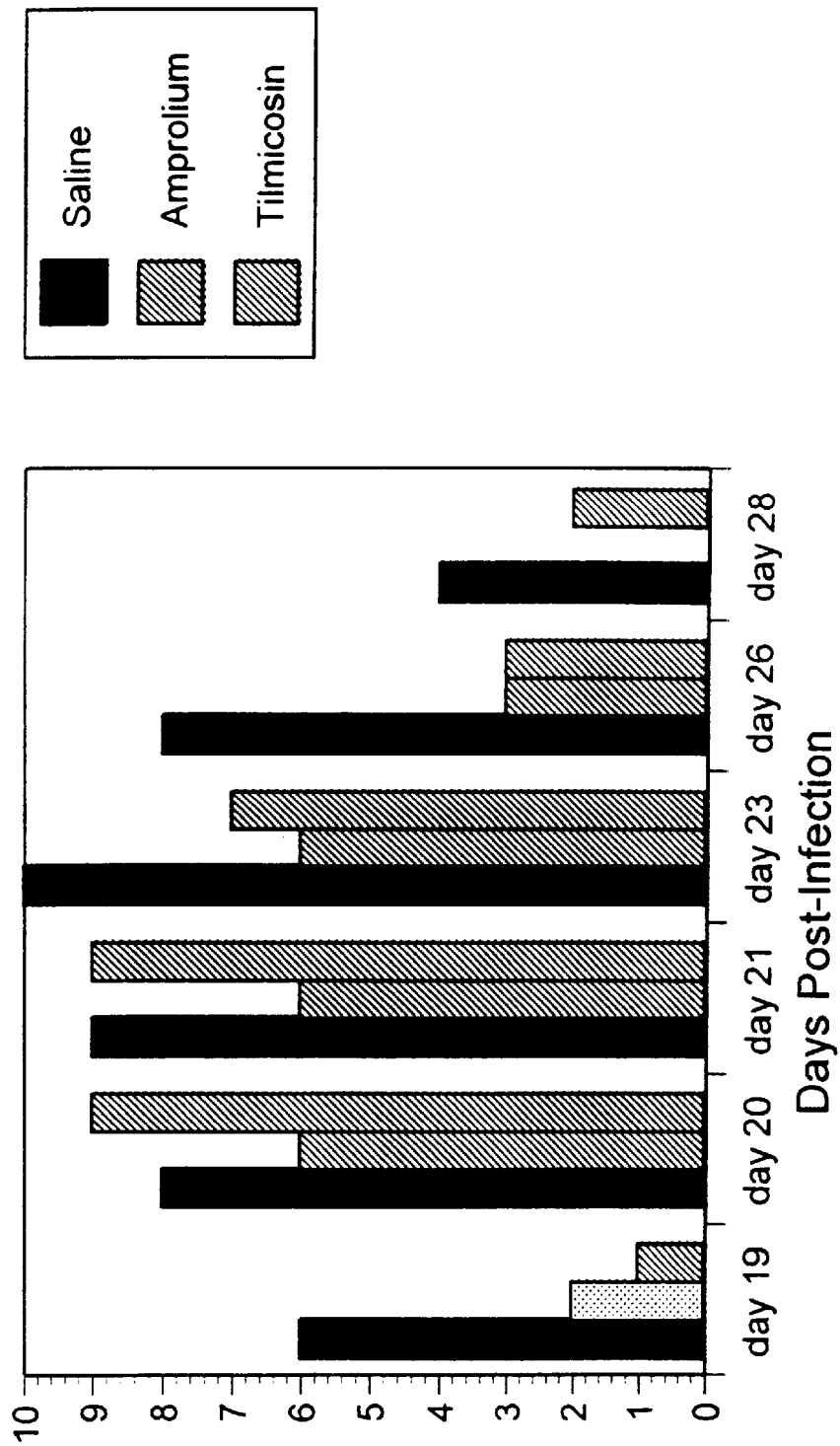
FIG. 10 shows the number of calves administered either tilmicosin or amprolium shedding oocysts per day (mean±SEM)
Figure 11:
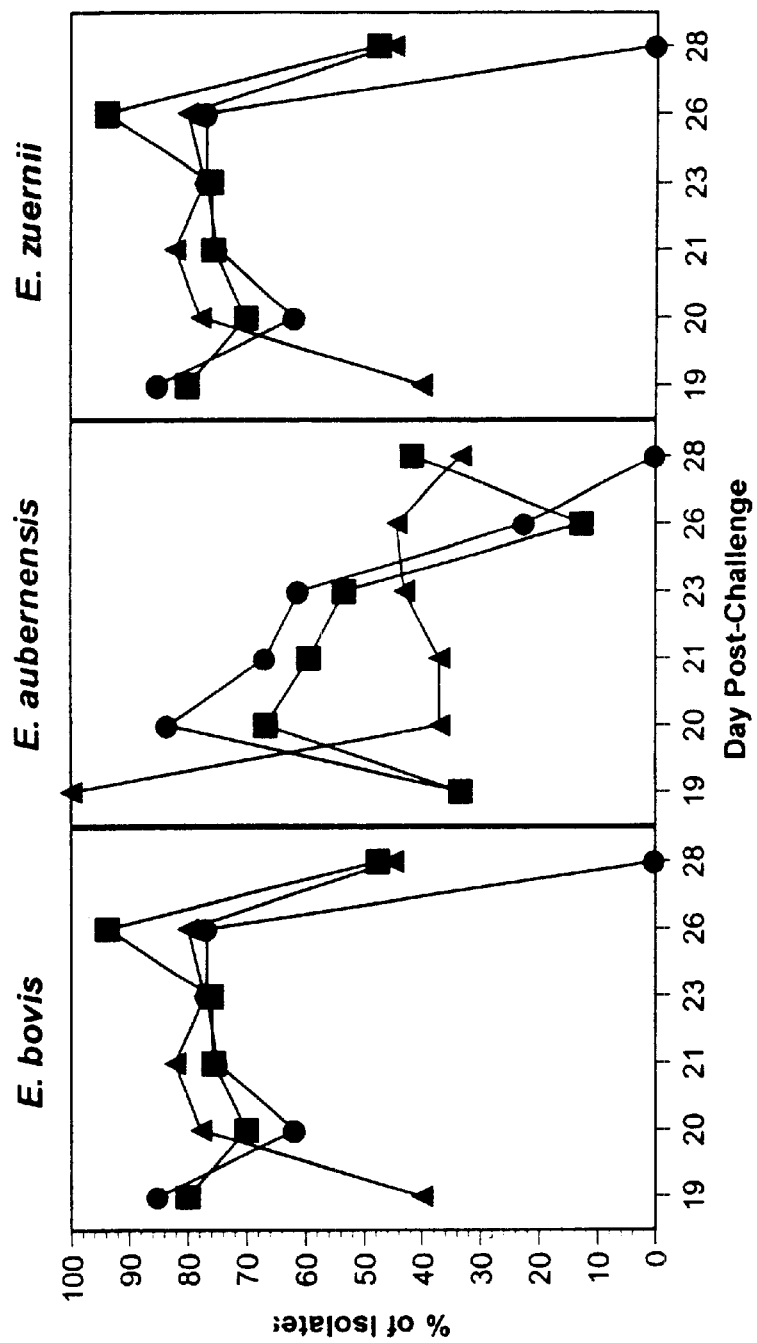
FIG. 11 shows the speciation profiles of calves experimentally infected with three Eimeria species.

All patents, patent applications, and publications cited herein are hereby incorporated by reference in their entireties.

Administration of macrolide antibiotics to bovine animals according to the invention is particularly advantageous in that it can also prevent development of other infections. Administration of preferred macrolide antibiotics according to the invention can prevent infection with respiratory disease causing organisms. It also can avoid the need for secondary drugs, such as lasalocid, decoquinate, monensin and other drugs that are otherwise conventionally used to treat or prevent coccidiosis.

Practice of the invention also avoids disadvantages associated with certain known treatments of coccidiosis, such as, e.g., toxicity and complicated dosing regimes. Furthermore, unlike certain conventional treatments, the antibiotic can be effectively administered in a single dose, although more than one dose can be administered if desired.

It has also been surprisingly determined that the macrolide antibiotics are as effective in treating coccidiosis as known anticoccidial agents, such as amprolium.

Furthermore, it has been determined that administration of the macrolide antibiotics according to the invention allows weight gain in the bovine animal that might not have been otherwise obtained It has also been determined that such administration reduces Eimeria oocyte shedding and diarrhea.

Any macrolide antibiotic can be employed in the practice of the invention. In a preferred embodiment, the invention relates to administration of a macrolide antibiotic of the azalide class. In one embodiment, the compound of Formula I is employed.

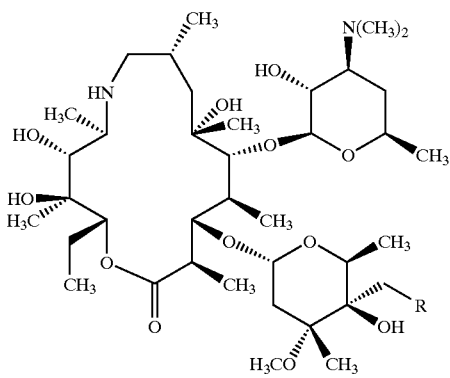

I wherein R is n-butylamino, 2-methoxyethylamino, piperidino, morpholino, t-butylamino, benzylamino, cyclopentylamino, propylamino, anilino, 2-methoxypropylamino, azido, hexylamino, 3-ethoxypropylamino, diethylamino, N-methylbutylamino, N-methylpropylamino, ethylamino, cyclopropylamino, ethylmethylamino, 2,2,2-trifluoroethylamino, allylamino, 2-hydroxyethylthio, dimethylamino, imidazol-1-yl, bis(2-hydroxyethyl)amino, pyrrolidino, 2-hydroxyethylmethylamino, 1,2,3-triazol-1-yl, 2-propynylamino, 2-methylimidazol-1-yl, diallylamino, or 1,2,4-triazol-1-yl. For example, an azalide antibiotic of the following formula is employed in the examples below:

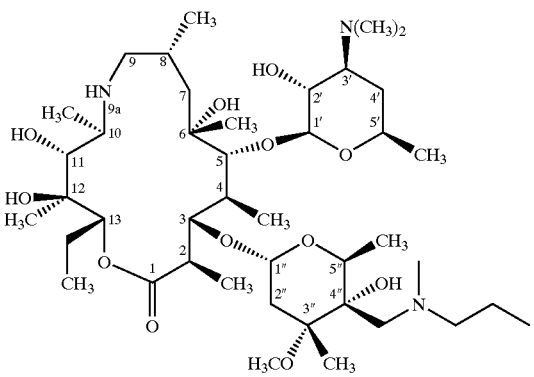

II

In another embodiment of the invention, the macrolide antibiotic employed is the commercially available compound, tilmicosin.

Macrolide antibiotics are well-known and available. The compound of Formula I is disclosed in WO98/56802, published Dec. 17, 1998, and can be prepared according to the methods described in that publication. Tilmicosin is commercially available, and its synthesis and formulation described, e.g., in U.S. Pat. No. 4,820,695 and 5,574,020.

The macrolide antibiotic can be administered to any bovine animal. In one embodiment, the bovine animal is a calf.

The Eimeria species treated is preferably *Eimeria bovis, Eimeria aubemensis,* or *Eimeria zuemii*.

The macrolide antibiotic is particularly useful in prevention of coccidiosis. "Prevention" encompasses administration to bovine animals carrying a causative organism of coccidiosis, but in whom the disease has not yet developed, such as animals entering a feedyard who are considered "at risk" of developing coccidiosis. "Prevention" also encompasses amelioration (as opposed to elimination) of symptoms of the disease. For example, in experiments described below, administration of macrolide antibiotic to cows already infected with Eimeria, i.e., a causative agent of coccidiosis, but who had not yet developed coccidiosis, was effective in ameliorating symptoms of the disease, although not necessarily in eliminating those symptoms.

The invention encompasses administration by, e.g., oral, parenteral, topical, and rectal routes. In one embodiment, the antibiotic is subcutaneously administered. The antibiotics may be administered alone or in combination with pharmaceutically acceptable carriers or diluents, and such administration may be carried out in single or multiple doses. More particularly, the active compounds may be administered in a wide variety of different dosage forms, i.e., they may be combined with various pharmaceutically acceptable inert carriers in the form of tablets, capsules, lozenges, troches, hard candies, powders, sprays, creams, salves, suppositories, jellies, gels, pastes, lotions, ointments, aqueous suspensions, injectable solutions, elixirs, syrups, and the like. Suitable carriers include, but are not limited to, solid diluents or fillers, sterile aqueous media and various non-toxic organic solvents. Oral pharmaceutical compositions can be suitably sweetened and/or flavored. In general, the active compounds are advantageously present in such dosage forms at concentration levels ranging from about 5.0% to about 70% by weight.

The compound is preferably administered to the bovine animals in a dosage of between 0.5 and 20, more preferably between 1 and 10, and most preferably between 2 and 5 g/kg of body weight.

For oral administration, tablets containing various excipients such as microcrystalline cellulose, sodium citrate, calcium carbonate, dicalcium phosphate and glycine may be employed along with various disintegrants such as starch (preferably corn, potato or tapioca starch), alginic acid and certain complex silicates, together with granulation binders like polyvinylpyrrolidone, sucrose, gelatin and acacia. Additionally, lubricating agents such as magnesium stearate, sodium lauryl sulfate and talc are often very useful for tabletting purposes. Solid compositions of a similar type may also be employed as fillers in gelatin capsules; preferred materials in this connection also include lactose or milk sugar as well as high molecular weight polyethylene glycols. When aqueous suspensions and/or elixirs are desired for oral administration, the active compound may be combined with various sweetening or flavoring agents, coloring matter or dyes, and, if so desired, emulsifying and/or suspending agents as well, together with such diluents as water, ethanol, propylene glycol, glycerin and various like combinations thereof.

For parenteral administration, solutions of an active compound in either sesame or peanut oil or in aqueous propylene glycol may be employed. The aqueous solutions should be suitably buffered (preferably pH 4.5–7) if necessary and the liquid diluent first rendered isotonic. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques will known to those skilled in the art.

It is also possible to administer the active compounds topically and this may be done by way of creams, jellies, gels, pastes, patches, ointments and the like, in accordance with standard pharmaceutical practice.

Suitable carriers and formulations are described, for example, in Remington's Pharmaceutical Sciences (16th edition, A. Oslow, ed., Mack, Easton, Pa. 1980).

If desired, the compound may be co-administered with any other compositions, including vaccines, nutrients, and medicaments. Examples of useful nutrient additives include vitamins, minerals, amino acids, sugars and fatty acids. Examples of useful medicaments include glycoproteins, antibiotics, antiparasitics, antivirals, probiotics, growth stimulators and sexual function modifiers. The compound administered according to the invention can also, if desired, be combined with administration of other compounds used to treat or prevent coccidia, including but not limited to sulfonamides such as sulfaquinoxaline or sulfamethazine, amprolium, lasalocid, decoquinate or monensin.

The invention also encompasses use of a pharmaceutically acceptable salt of a macrolide antibiotic. Pharmaceutically acceptable salts include salts of acidic or basic groups which may be present in the compounds. Compounds that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)] salts. Compounds that include an amino moiety may form pharmaceutically acceptable salts with various amino acids, in addition to the acids mentioned above.

Compounds employed that are acidic in nature are capable of forming base salts with various pharmacologically acceptable cations. Examples of such salts include the alkali metal or alkaline earth metal salts and, particularly, the calcium, magnesium, sodium and potassium salts of the compounds.

The following examples are illustrative only, and not intended to limit the scope of the present invention.

EXAMPLE 1

Administration of an azalide macrolide antibiotic according to the invention was compared with administration of amprolium, a commercially available agent, and saline control solution, in preventing full development of coccidiosis in Eimeria challenged calves.

| MATERIALS | | |
|---|---|---|
| 1. | Compound: | Sterile 0.9% sodium chloride Elkins-Sinn, Inc. |
|  | Dosage form: | Injectable, U.S.P. |
| 2. | Compound: | Corid ® 20% soluble powder (amprolium), Merck Ag. Vet. |
|  | Dosage form: | Oral, water soluble |
|  | Potency: | 20% soluble solution (3 oz./1 quart water) administered 1 fl. oz./100 lbs. |
|  | Formulation: | Commercial |
| 3. | Compound name | Azalide antibiotic of Formula II |
|  | Dosage form: | injectable |
|  | Potency: | 200 mg/ml |
|  | Formulation: | 25% propylene glycol vehicle (pH adjusted 5.0 ± 0.5 with citric acid) |

| Summary Of Experimental Design | |
|---|---|
| Treatment | # Animals |
| 1) Sterile saline, 1 ml/30 kg, SIDX1, SC | 8 |
| 2) Corid ®, (amprolium) 20% soluble powder, (5 days in water) | 8 |
| 3) Compound of Formula II 5 mg/kg, SIDX1, SC | 8 |
| 4) Compound of Formula II 2.5 mg/k, SIDX1, SC | 8 |

SC = subcutaneous;
SID = single injection daily

Procedure

Eighty naive calves weighing approximately 110–125 kg were housed in twenty holding pens (4 animals/pen) 16 days prior to study initiation. The pens had a previous history of recurring natural coccidia infections. The calves were acclimated in order to facilitate coccidial exposure and allow time for clinical signs to develop. On day 14, with no signs of naturally occurring coccidiosis in the calves, each calf was challenged orally with a mixed culture of bovine coccidia (*Eimeria bovis*~90% and *Eimeria aubumenis*~10%). Calves were each also challenged orally with $1.25 \times 10^7$ oocysts and observed for signs of clinical disease. On day 23 post-challenge, calves began to show signs of clinical disease and fecal samples were taken to determine oocyst shedding. Calves which exhibited a positive fecal sample for oocyst shedding and a fecal consistency score of >2 (which corresponds to moderate diarrhea) were employed in the experiment.

Calves were randomly allotted to one of six treatment groups. They were weighed at allotment and treatments administered subcutaneously in the pre-scapular region of the neck. Amprolium was administered by drench dosing (SID×5) beginning on the day of allotment.

Rectal temperatures were determined and recorded at approximately the same time each day for the 21 day duration of the study. Attitude, hydration and fecal consistency scores were evaluated daily. Daily fecal samples were taken for qualitative analysis of the shedding of oocysts. Mortalities were necropsied and gross findings were recorded.

At termination of the experiment, surviving animals were weighed, euthanized, and post-mortem examinations conducted.

Results

Description of Disease Outbreak—A natural outbreak of coccidiosis did not occur during the acclimation period. As a result, the calves were inoculated orally with coccidia oocysts. Twenty-three days post-inoculation, calves began showing typical signs of clinical coccidiosis and oocyst shedding.

Rectal Temperature—Mean daily rectal temperatures for each treatment are shown below. Mean daily rectal temperatures remained in the normal range during the duration of the study. No significant differences were seen between the treatment groups.

Clinical Scores—Clinical score assessments include scores for fecal consistency, hydration and attitude. Score assessments are presented below. Attitude, hydration and fecal scores indicate calves administered amprolium and azalide compounds responded favorably to treatment compared with the saline treated calves.

Fecal Consistency—Mean daily fecal consistency scores are shown below. Amprolium and the compound of Formula II (5 and 2.5mg/kg) displayed statistically significant reductions (p>0.05) in mean daily fecal consistency scores compared to the saline treated calves. No significant differences in scores were seen between the amprolium and azalide (compound of Formula II) treated calves.

Hydration Scores—Mean daily hydration scores are shown below. Calves administered the compound of Formula II (5 and 2.5mg/kg) displayed statistically significant reductions (p>0.05) in mean daily hydration scores compared to the saline treated calves. No significant differences in hydration scores were seen between the amprolium and azalide treated calves.

Attitude Scores—Mean daily attitude scores are shown below. Treatment of calves with amprolium, and the compound of Formula II (5 and 2.5 mg/kg) resulted in significant reductions (p>0.05) in mean daily attitude scores compared to the saline controls. Attitude scores were significantly reduced 24 hours post-treatment and remained noticeably reduced through the duration of the study. No significant differences were seen between the amprolium and azalide treatment groups.

Mortality Rates—Mortality rates are summarized in Table 1. Two calves (one of the saline controls and one treated with amprolium) died due to coccidiosis in this study. Both calves died within 24 hours of dosing, suggesting the infection was well established prior to dosing. There were no mortalities among animals treated with the azalide.

TABLE 1

Effects of administration of either amprolium or the compound of Formula II upon the mortality rates of calves infected with *bovine coccidia*.

| Treatment | Mortality Rates |
|---|---|
| Saline | 1/8 (13%) |
| Amprolium | 1/8 (13%) |
| Compound of Formula II (5 mg/kg) | 0/8 (0%) |
| Compound of Formula II (2.5 mg/kg) | 0/8 (0%) |

Weight Gain—Table 2 summarizes the effects of administration upon 21 day weight gains. Positive weight gains were seen in all treatment groups. Numerical increases in weight gain were seen with azalide treated animals compared to the saline controls.

TABLE 2

Effects of administration of either amprolium or the compound of Formula II upon 21 day average daily gain for calves infected with *bovine coccidia*.

| Treatment | 21 Day Average Daily Gain (kg) |
|---|---|
| Saline | 0.60 |
| Amprolium | 0.75 |
| Compound of Formula II (5 mg/kg) | 0.79 |
| Compound of Formula II (2.5 mg/kg) | 1.03 |

Parasitology—Eimeria oocyst shedding was monitored daily post-treatment. Table 3 summarizes the proportion of animals that ceased oocyst shedding beginning day 6 post-dosing. A significant increase (p>0.05) in the number of animals that ceased oocyst shedding was seen following treatment with either amprolium or the compound of Formula II (5 and 2.5mg/kg) when compared to the saline treated calves. No significant differences were noted between the responses of the amprolium and azalide treatment groups.

TABLE 3

Proportion of infected calves that ceased oocyst shedding 6 days post-treatment with either amprolium or the compound of Formula II.

| Treatment | Ceased Oocyst Shedding (6 days post-treatment) |
|---|---|
| Saline | 0/7 (0%) |
| Amprolium | 7/7 (100%) |
| Compound of Formula II (5 mg/kg) | 7/8 (88%) |
| Compound of Formula II (2.5 mg/kg) | 7/8 (88%) |

Necropsy Gross Findings—The two calves which died due to coccidiosis in this study displayed classical signs of bloody intestines with sloughed epithelial tissue evident. Test animals that were administered saline and euthanized at the termination of the study showed signs of mild colitis at necropsy. The majority of the test animals displayed no visible lesions at necropsy.

Conclusions

Animals administered amprolium and the compound of Formula II displayed improved clinical responses (clinical scores, weight gain and oocyst shedding) compared to the saline control group. The improvements in clinical parameters indicated that these compounds provided effective control of coccidial infection in this study. The compound of Formula II displayed efficacy that was comparable to that of amprolium, with a less complicated dosing regimen.

EXAMPLE 2

Administration of amprolium was compared with tilmicosin, a commercially available macrolide antibiotic, in the prevention of coccidiosis in Eimeria challenged calves.

| | Materials | |
|---|---|---|
| 1. | Compound: | Sterile 0.9% sodium chloride (saline) Elkins-Sinn, Inc. |
| | Dosage form: | Injectable, U.S.P. |
| 2. | Compound: | Corid ® 20% soluble powder (amprolium), Merck Ag. Vet., |
| | Dosage form: | Oral, water-soluble |
| | Potency: | 20% soluble solution: (3 oz./1 quart water) administered 1 fl. oz./100 lbs. |
| | Formulation: | Commercial |
| 3. | Compound: | Tilmicosin |
| | Dosage form: | Injectable |
| | Potency: | 300 mg/ml |
| | Formulation: | Commercial |

| Summary Of Experimental Design: | |
|---|---|
| Treatment | # Animals |
| 1) Sterile saline, 1 ml/30 kg, SIDX1, SC | 10 |
| 2) Corid ® (amprolium), 9.6% Oral Solution 10 mg/kg, (5 days in water-drench dosing) | 10 |
| 3) Tilmicosin 10 mg/kg SIDX1, SC | 10 |

SC = subcutaneous;
SID = single injection daily)

Procedure

Sixty naive calves were housed in five holding pens (12 animals/pen). Calves were held 7 days prior to challenge in order to acclimate to the facility. On days −6, −4, and −2 pre-challenge fecal samples were obtained for semi-quantitative oocyst counts. On day −4 pre-challenge, oocysts were speciated if present. On day 0 calves were inoculated orally with the Eimeria culture. Temperatures were determined and recorded at approximately the same time each day for the duration of the study. Attitude, hydration and fecal consistency scores were evaluated daily. Post-challenge, fecal samples were collected on days 2, 4, 6, 8 and 10. Oocysts were speciated on day 10 post-challenge.

On day 10 post-challenge, each of fifty animals was randomly allotted to one of five treatment groups. Agents were either administered subcutaneously in the pre-scapular region of the neck or drench dosed orally.

Post-treatment, fecal samples were taken for semi-quantitative analysis of the shedding of coccidia oocysts on days 12, 14, 16 and 18. Beginning on day 19 and continuing through day 28, daily fecal samples were evaluated for semi-quantitative counts. Speciation of shed oocysts was performed on days 19–21, 23, 26 and 28.

Calves dying during the course of the study or euthanized due to a moribund condition associated with clinical coccidiosis were considered mortalities. Mortalities were necropsied and gross findings were recorded. At study termination (day 28), all remaining animals were weighed, euthanized, and post mortem examinations conducted.

Results

Description of Disease Outbreak—Calves were inoculated orally with 2 ml of a coccidia challenge containing 125,000 sporulated oocysts with a species percent count of 93% E. bovis, 4% E. aubumenis and 3% E. zuemii coccidia oocysts. At 19 days post-challenge, oocyst shedding was detected.

Rectal Temperature—Mean daily rectal temperatures for each treatment are presented below. Mean daily rectal temperatures remained in the normal range during the duration of the study. No significant differences ($p > 0.05$) were seen between the agents administered.

Clinical Scores—Clinical score assessments included scores for fecal consistency, hydration and attitude. Attitude and fecal scores indicated calves administered tilmicosin and amprolium responded favorably to treatment as compared with the saline treated calves. Increases in fecal scores, hydration scores and attitude scores corresponded to the time of detectable shedding of oocysts (19 days).

Fecal Consistency—Mean daily fecal consistency scores obtained are shown below. Amprolium and tilmicosin displayed statistically significant reductions ($p \leq 0.05$) in mean daily fecal consistency scores as compared with the saline treated calves. The increased fecal scores occurred 2–3 days prior to shedding of oocysts and remained elevated throughout the 28 day study. No statistically significant ($p > 0.05$) differences in fecal consistency scores were seen between the amprolium and tilmicosin treated calves.

Hydration Scores—Mean daily hydration scores obtained are shown below. Calves administered amprolium and tilmicosin displayed reductions in mean daily hydration scores compared to the saline treated calves.

Attitude Scores—Mean daily attitude scores obtained are shown below. Treatment of calves with amprolium and tilmicosin resulted in significant reductions ($p \leq 0.05$) in mean daily attitude scores compared to the saline controls. The differences in attitude scores were noted between the amprolium and saline calves at the time of peak oocyst shedding. Animals administered tilmicosin exhibited numerical reductions in attitude scores relative to the saline controls during the last seven days of the study. No statistically significant ($p > 0.05$) differences were seen between the tilmicosin and amprolium treatment groups.

Mortality Rates—Mortality rates obtained are summarized in Table 4. Five calves died due to coccidiosis. Three calves died on day 23 post-infection and two calves died day 28 post-infection. Two animals died in both the saline and tilmicosin treatment groups. One animal treated with amprolium died. There were no statistically significant ($p > 0.05$) differences in mortality rates among the animals administered either tilmicosin or amprolium.

TABLE 4

Effects of treatment upon the mortality rates of calves infected with *bovine coccidia*.

| Treatment | Mortality Rates |
|---|---|
| Saline | 2/10 (20%) |
| Amprolium | 1/10 (10%) |
| Tilmicosin | 2/10 (20%) |

Weight Gain—Table 5 summarizes the effects of treatment upon weight gains. Positive average daily gains were seen in all treatment groups. Numerical increases in weight gain were seen with treatment with amprolium as compared with saline and tilmicosin. Tilmicosin and saline treated animals responded similarly with respect to the 21 day average daily gains.

TABLE 5

Effects of treatment upon 21 day average daily gain for calves infected with *bovine coccidia*.

| Treatment | 21 Day Average Daily Gain (kg) |
|---|---|
| Saline | 0.30 |
| Amprolium | 0.60 |
| Tilmicosin | 0.21 |

Parasitology—Eimeria oocyst shedding was monitored prior to challenge and post-challenge. Oocyst shedding during the experiment is shown below. Oocyst shedding was first detectable on day 19 post-challenge. Statistically significant ($p \leq 0.05$) increases in oocyst shedding were seen in saline treated animals as compared to the tilmicosin and amprolium treated animals. No statistically significant ($p > 0.05$) differences in oocyst shedding were seen between tilmicosin and amprolium treated calves.

Speciation Results—The number of animals per treatment group shedding oocysts on days 19, 20, 21, 23, 26 and 28 post-infection is shown below. 40–100% of the animals treated with saline consistently shed oocysts each day. Animals administered amprolium or tilmicosin displayed decreased oocyst shedding as compared with the saline controls. The speciation profiles for each Eimeria species detected in the fecal samples per day of shedding are also shown below. *E. bovis* accounted for ~60–100% of the oocysts shed per sample. *Eimeria aubumenis* and *Eimeria zuemii* accounted for ~10–40% of the shed oocysts per sample. At day 28 post-infection there was an apparent increase in the shedding of *E. zuemii*, resulting in a corresponding decrease in the shedding of *E bovis*. Over the entire shedding period monitored, none of the compounds tested appeared to significantly alter the speciation profiles of shed oocysts.

Necropsy Gross Findings—At necropsy, the majority of the animals displayed gross pathology consistent with a moderate to severe coccidial infection. In this study, calves from all treatment groups showed signs of hemorrhagic ilietis and colitis. Fourteen percent of the calves in this study (7/50) displayed no gross pathology at necropsy. However, calves from each of these treatment groups shed oocyst during the study, suggesting some level of coccidia infection in these animals.

Clinical Discussion—Oral inoculation of the Eimeria challenge resulted in shedding of oocysts beginning 19 days post-infection. *Eimeria bovis* was the prominent species shed in all groups. However, *Eimeria aubumenis* and *Eimeria zuemii* were shed in lesser quantities by calves in all groups. The induced coccidia challenge in this study resulted in 5 mortalities. Two mortalities occurred in the saline and tilmicosin treated calves and one animal died that was administered amprolium.

Conclusions

Tilmicosin and amprolium displayed improved clinical responses and decreased oocyst shedding as compared to saline treated animals.

What is claimed is:

1. A method of treating coccidiosis in a bovine animal by administering, when clinical signs of coccidiosis infection exist, to an animal an effective amount of an azalide macrolide antibiotic of the following formula:

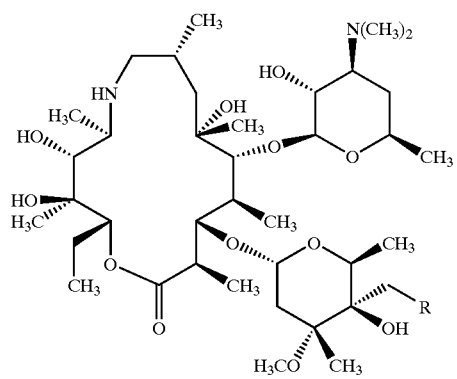

I wherein R is n-butylamino, 2-methoxyethylamino, piperidino, morpholino, t-butylamino, benzylamino, cyclopentylamino, propylamino, anilino, 2-methoxypropylamino, azido, hexylamino, 3-ethoxypropylamino, diethylamino, N-methylbutylamino, N-methylpropylamino, ethylamino, cyclopropylamino, ethymethylamino, 2,2,2-trifluoroethylamino, pyrrolidino, 2-hydroxy-ethylmethylamino, 1,2,3-triazol-1-yl, 2-propynylamino, 2-methylimidazol-1-yl, diallylamino, or 1,2,4-triazol-1-yl.

2. A method of treating coccidiosis in a bovine animal by administering, when clinical signs of coccidiosis infection exist, to an animal an effective amount of an azalide macrolide antibiotic of the following formula:

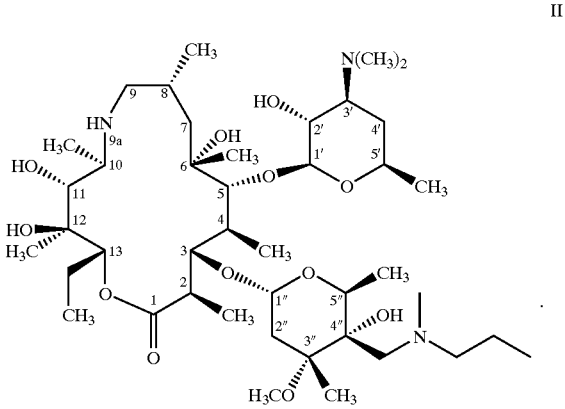

II

3. The method according to claim 1 wherein the azalide macrolide antibiotic is administered in an amount that increases weight gain in the bovine animal.

4. The method according to claim 1 wherein the coccidiosis results from infection from *Eimeria bovis E. aubemensis* or *Eimeria zuemii*.

5. The method according to claim 1 wherein said administration reduces *Eimeria oocyte* shedding or diarrhea.

6. The method according to claim 1 wherein the azalide macrolide antibiotic is administered to the bovine animal in a dosage of between 0.5 and 20 g/kg of body weight.

* * * * *